United States Patent
Heneghan et al.

(10) Patent No.: US 6,624,117 B1
(45) Date of Patent: Sep. 23, 2003

(54) HEAT SENSITIVE RECORDING MATERIAL

(75) Inventors: Michael Heneghan, Rheinfelden-Adelhausen (DE); Roy Alan Kirk, Manchester (GB); James Philip Taylor, Macclesfield (GB); John Whitworth, Manchester (GB); Robert Montgomery O'Neil, Manchester (GB); John Barry Henshall, Manchester (GB)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/868,105
(22) PCT Filed: Dec. 3, 1999
(86) PCT No.: PCT/EP99/09473
§ 371 (c)(1), (2), (4) Date: Oct. 1, 2001
(87) PCT Pub. No.: WO00/35679
PCT Pub. Date: Jun. 22, 2000

(30) Foreign Application Priority Data

Dec. 16, 1998 (GB) .............................. 9827569

(51) Int. Cl.$^7$ .............................. B41M 5/20; B41M 5/24
(52) U.S. Cl. ........................ 503/216; 503/209; 514/592; 514/596; 514/597; 514/598
(58) Field of Search ................ 503/216, 225, 503/209; 427/150, 151; 514/592, 596, 597, 598

(56) References Cited

FOREIGN PATENT DOCUMENTS

| EP | 0526072 | 2/1993 |
| EP | 0535887 | 4/1993 |
| EP | 0701905 | 3/1996 |
| EP | 0738610 | 10/1996 |
| EP | 0832757 | 4/1998 |
| EP | 0860738 | 8/1998 |

OTHER PUBLICATIONS

Patent Abstracts of Japan, vol. 1997, No. 3, (1997) for JP 08295081.
Patent Abstracts of Japan, vol. 1998, No. 08, (1998) for JP 10058836.
F. Briganti et al., European Journal of Medicinal Chemistry, vol. 32, No. 11, (1997), pp. 901–910.
C. T. Supuran et al., European Journal of Medicinal Chemistry, vol. 33, No. 10, (1998).
C. T. Supuran et al., Journal of Enzyme Inhibition, vol. 13, No. 4, (1998), pp. 291–310.

*Primary Examiner*—Bruce H. Hess
(74) *Attorney, Agent, or Firm*—Kevin T. Mansfield

(57) ABSTRACT

A heat sensitive recording material, comprising
a) at least one colour forming compound, and
b) at least one developer of the formula

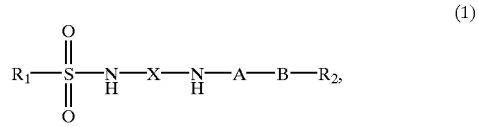

(1)

wherein
$R_1$ is unsubstituted or substituted phenyl, naphthyl or $C_1$–$C_{20}$alkyl,
X is a group of the formula

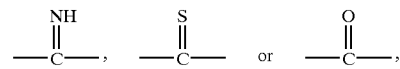

A is unsubstituted or substituted phenylene, naphthylene or $C_1$–$C_{12}$alkylene, or is an unsubstituted or substituted heterocyclic group,
B is a linking group of formula —O—SO$_2$—, —SO$_2$—O—, —NH—SO$_2$—, —SO$_2$—NH—, —S—SO$_2$—, —O—CO—, —O—CO—NH—, —NH—CO—, —NH—CO—O—, —S—CO—NH—, —S—CS—NH—, —CO—NH—SO$_2$—, —O—CO—NH—SO$_2$—, —NH=CH—, —CO—NH—CO—, —S—, —CO—, —O—, —SO$_2$—NH—CO—, —O—CO—O— and —O—PO—(OR$_2$)$_2$, and
$R_2$ is unsubstituted or substituted aryl or benzyl or $C_1$–$C_{20}$alkyl,
with the proviso, that, if B is not a linking group of formula —O—SO$_2$—, $R_2$ is unsubstituted or substituted phenyl, naphthyl or $C_1$–$C_8$alkyl and that, if B is —O—, $R_2$ is not alkyl.

23 Claims, No Drawings

HEAT SENSITIVE RECORDING MATERIAL

The present invention relates to heat sensitive recording materials. It more particularly relates to such recording material in the form of a supporting substrate, for example, a paper sheet, synthetic paper sheet or plastic resin film coated with colour-forming systems comprising a colorless or pale coloured electron donative compound (colour forming compound) and an organic electron acceptor (developer).

Heat sensitive recording has conventionally been used as a system for recording transferred information through the mediation of heat, by utilising a colour reaction between a colour forming compound and a developer.

The properties which are most desirable in a colour forming material, in addition to the effective development of colour, are thermal response, background whiteness and image stability, especially light fastness of the developed colour, heat and moisture fastness of the developed colour, oil fastness of the developed colour, plasticiser resistance of the developed colour and water fastness of the developed colour.

A need exists to improve the above properties and to improve the archival capabilities of such recording materials. It is an object of the present invention to provide heat sensitive recording materials with improved properties, especially to provide an increase in image stability whilst improving the background whiteness of the paper before imaging and the background whiteness of the undeveloped portion after imaging.

The present invention is directed to a heat sensitive recording material, comprising a) at least one colour forming compound, and
b) at least one developer of the formula

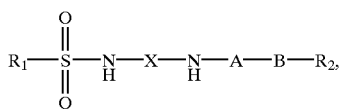   (1)

wherein $R_1$ is unsubstituted or substituted phenyl, naphthyl or $C_1$–$C_{20}$alkyl, X is a group of the formula

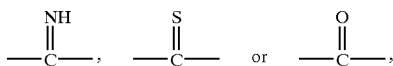

A is unsubstituted or substituted phenylene, naphthylene or $C_1$–$C_{12}$alkylene, or is an unsubstituted or substituted heterocyclic group, B is a linking group of formula —O—SO$_2$—, —SO$_2$—O—, —NH—SO$_2$—, —SO$_2$—NH—, —S—SO$_2$—, —O—CO—, —O—CO—NH—, —NH—CO—, —NH—CO—O—, —S—CO—NH—, —S—CS—NH—, —CO—NH—SO$_2$—, —O—CO—NH—SO$_2$—, —NH=CH—, —CO—NH—CO—, —S—, —CO—, —O—, —SO$_2$—NH—CO—, —O—CO—O— and —O—PO—(OR$_2$)$_2$, and $R_2$ is unsubstituted or substituted aryl or benzyl or $C_1$–$C_{20}$alkyl, with the proviso, that, if B is not a linking group of formula —O—SO$_2$—, $R_2$ is unsubstituted or substituted phenyl, naphthyl or $C_1$–$C_8$alkyl and that, if B is —O—, $R_2$ is not alkyl.

$R_1$ as phenyl or naphthyl can be unsubstituted or substituted by, for example, $C_1$–$C_8$alkyl, $C_1$–$C_8$alkoxy or halogen. Preferred substituents are $C_1$–$C_4$alkyl, especially methyl or ethyl, $C_1$–$C_4$alkoxy, especially methoxy or ethoxy, or halogen, especially chlorine. $R_1$ as naphthyl is preferably unsubstituted. $R_1$ as phenyl is preferably substituted, especially by one of the above alkyl substituents.

$R_1$ as $C_1$–$C_{20}$alkyl can be unsubstituted or substituted by, for example $C_1$–$C_8$alkoxy or halogen. Preferred substituents are $C_1$–$C_4$alkoxy, especially methoxy or ethoxy, or halogen, especially chlorine. $R_1$ as $C_1$–$C_{20}$alkyl is preferably unsubstituted.

Preferably, $R_1$ is phenyl which is unsubstituted or substituted by $C_1$–$C_8$alkyl, $C_1$–$C_8$alkoxy or halogen. Of most importance are the substituted phenyl groups. Highly preferred are phenyl groups which are substituted by $C_1$–$C_4$alkyl, preferably by methyl.

X is preferably a group of the formula

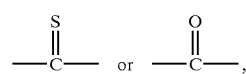

especially a group of the formula

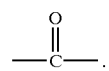

A as a phenylene or naphthylene group can be unsubstituted or substituted by, for example, $C_1$–$C_8$alkyl, halogen-substituted $C_1$–$C_8$alkyl, $C_1$–$C_8$alkoxy-substituted $C_1$–$C_8$alkyl, $C_1$–$C_8$alkoxy, halogen-substituted $C_1$–$C_8$alkoxy, $C_1$–$C_8$alkylsulphonyl, halogen, phenyl, phenoxy or phenoxycarbonyl. Preferred alkyl and alkoxy substituents are those containing 1 to 4 carbon atoms. Preferred substituents are $C_1$–$C_8$alkyl, halogen-substituted $C_1$–$C_8$alkyl, $C_1$–$C_8$alkyl-sulphonyl or halogen. A as a naphthylene group is preferably unsubstituted.

A as a heterocyclic group is preferably pyrimidylene which is unsubstituted or substituted by $C_1$–$C_8$alkyl, especially by $C_1$–$C_4$alkyl.

A as a $C_1$–$C_{12}$alkylene group is preferably $C_1$–$C_8$alkylene, especially $C_1$–$C_4$alkylene.

Preferred groups A are phenylene groups which are unsubstituted or substituted by $C_1$–$C_8$alkyl, halogen-substituted $C_1$–$C_8$alkyl, $C_1$–$C_8$alkoxy-substituted $C_1$–$C_8$alkyl, $C_1$–$C_8$alkoxy, halogen-substituted $C_1$–$C_8$alkoxy, $C_1$–$C_8$alkylsulphonyl, halogen, phenyl, phenoxy or phenoxycarbonyl, especially $C_1$–$C_8$alkyl, halogen-substituted $C_1$–$C_8$alkyl, $C_1$–$C_8$alkylsulphonyl or halogen.

Highly preferred groups A are phenylene groups which are unsubstituted or substituted by $C_1$–$C_4$alkyl or halogen, especially unsubstituted phenylene groups.

Preferred linking groups B are those of formulae —O—SO$_2$—, —SO$_2$—O—, —SO$_2$—NH—, —S—SO$_2$—, —O—, —O—CO— and —O—CO—NH—, especially linking groups of formulae —O—SO$_2$—, —SO$_2$—O— and —SO$_2$—NH—. Highly preferred are the linking groups B of formula —O—SO$_2$— and —O—.

$R_2$ as aryl is preferably phenyl or naphthyl which can be unsubstituted or substituted by, for example, $C_1$–$C_8$alkyl, halogen-substituted $C_1$–$C_8$alkyl, $C_1$–$C_8$alkoxy-substituted $C_1$–$C_8$alkyl, $C_1$–$C_8$alkoxy, halogen-substituted $C_1$–$C_8$alkoxy or halogen. Preferred alkyl and alkoxy substituents are those containing 1 to 4 carbon atoms. Preferred substituents are $C_1$–$C_4$alkyl and halogen. $R_2$ as naphthyl is preferably unsubstituted.

$R_2$ as benzyl can be substituted by the substituents given for $R_2$ as phenyl or naphthyl. Unsubstituted benzyl is preferred.

$R_2$ as $C_1$–$C_{20}$alkyl is preferably $C_1$–$C_8$alkyl, especially $C_1$–$C_6$alkyl, and can be unsubstituted or substituted by, for example, $C_1$–$C_8$alkoxy, halogen, phenyl or naphthyl. Preferred are the unsubstituted alkyl groups, especially $C_1$–$C_4$alkyl.

Preferred groups $R_2$ are $C_1$–$C_6$alkyl; halogen-substituted $C_1$–$C_6$alkyl; phenyl-substituted $C_1$–$C_6$alkyl; naphthyl-substituted $C_1$–$C_6$alkyl; phenyl which is unsubstituted or substituted by $C_1$–$C_8$alkyl, halogen-substituted $C_1$–$C_8$alkyl, $C_1$–$C_8$alkoxy-substituted $C_1$–$C_8$alkyl, $C_1$$C_8$alkoxy, halogen-substituted $C_1$–$C_8$alkoxy or halogen; naphthyl and benzyl which is substituted by $C_1$–$C_4$alkyl or halogen.

Highly preferred groups $R_2$ are $C_1$–$C_4$alkyl; halogen-substituted $C_1$–$C_4$alkyl; phenyl which is unsubstituted or substituted by $C_1$–$C_4$alkyl or halogen; naphthyl and benzyl which is unsubstituted or substituted by $C_1$–$C_4$alkyl or halogen, especially phenyl which is unsubstituted or substituted by $C_1$–$C_4$alkyl.

Preferred are developers of formula (1), wherein.

$R_1$ is phenyl which is substituted by $C_1$–$C_4$alkyl, preferably by methyl,

X is a group of the formula

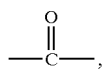

A is phenylene which is unsubstituted or substituted by $C_1$–$C_8$alkyl or halogen, preferably unsubstituted phenylene, like 1,3-phenylene, B is a linking group of formula —O—$SO_2$— or —O— and $R_2$ is phenyl, naphthyl or benzyl which is unsubstituted or substituted by $C_1$–$C_4$alkyl or halogen, especially phenyl which is substituted by $C_1$–$C_4$alkyl.

The compounds of formula (1) can be prepared in accordance with schemes 1–3 below;

1.

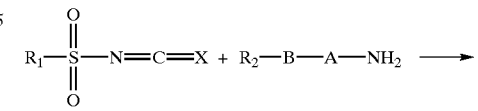

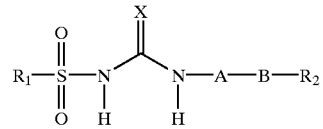

2.

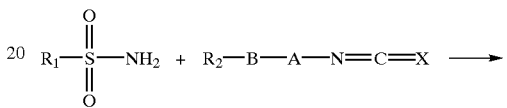

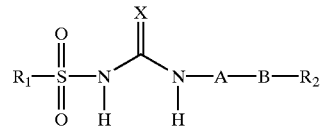

3.

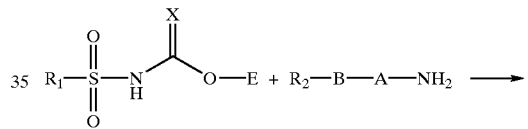

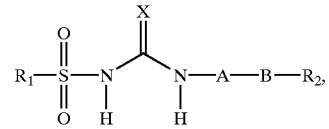

where $R_1$, $R_2$, A, B and X are as defined above and E is alkyl or aryl.

Furthermore, in the case where the species $H_2N$—A—B—H is available the compounds of formula (1) can be prepared in accordance with scheme 4 below;

4.

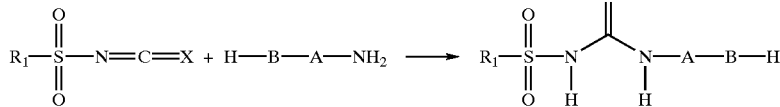

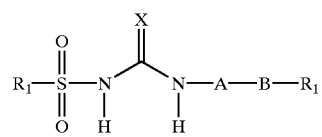

In the case of schemes 1, 2 and 4 the R₁-sulphonylisocyanate (or R₁-sulphonamide) is reacted with R₂-amine (or R₂-isocyanate) in the presence or absence of an organic solvent. Preferably in the presence of an (apolar or polar) aprotic solvent such as aromatic hydrocarbons, chlorinated aromatic hydrocarbons, aliphatic or alicyclic hydrocarbons, chlorinated hydrocarbons, dialkylacylamides, aliphatic esters, aliphatic ketones, alicyclic ketones, aliphatic ethers, cyclic ethers, alkylnitriles and mixtures thereof. Most preferred are toluene, xylenes, petroleum ether, cyclohexane, dimethyl formamide, dimethylacetamide, ethylacetate, propyl acetate, butylacetate, diethylether, dibutylether, tetrahydrofuran, acetone, butanone, cyclohexanone, nitromethane, acetonitrile, propionitrile, nitromethane, ethyleneglycoldimethylether, chloroform, dichloromethane, carbon tetrachloride, chlorobenzene, dichlorobenzene, dioxan or mixtures thereof. Polar protic solvents such as alcohols may also be used. The reaction is preferably carried out at 0–100° C. preferably 0–40° C. for up to 12 hours. The reaction may further be catalysed by tertiary amines, carboxylic acids, amides or ureas.

In the case of scheme 3, the reaction of carbamate $R_1SO_2NHCXOE$ with amine $R_2BANH_2$ may be carried out in excess amine, water, organic solvent or mixture thereof in the presence or absence of an inorganic or organic base. Typical solvents include those discussed hereinbefore. Bases used include alkali metal carbonates ($K_2CO_3$, $Na_2CO_3$), alkali metal hydroxides (NaOH, KOH), alkali metal alkoxides (sodium methoxide), pyridine, tertiary amines such as triethylamine, diisopropylethylamine.

Many syntheses are known for sulphonyl ureas and are incorporated herein by reference (J.Med.Chem., 1990, (33), 9, 2393, Chem.Rev., 1952, (50), 1, Chem.Rev., 1965, (65), 365).

In addition, the present invention is directed to novel compounds of formula

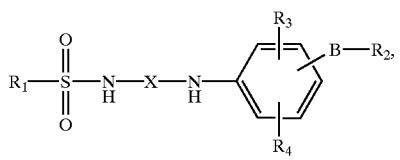

(2)

wherein $R_1$ is unsubstituted or substituted phenyl, naphthyl or $C_1$–$C_{20}$alkyl, $R_3$ and $R_4$ independently of each other are hydrogen, $C_1$–$C_8$alkyl, halogen-substituted $C_1$–$C_8$alkyl, $C_1$–$C_8$alkoxy-substituted $C_1$–$C_8$alkyl, $C_1$–$C_8$alkoxy, halogen-substituted $C_1$–$C_8$alkoxy, $C_1$–$C_8$alkylsulphonyl, halogen, phenyl, phenoxy or phenoxycarbonyl, X is a group of the formula

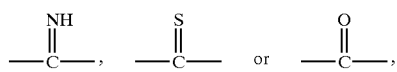

B is a linking group of formula —O—$SO_2$—, —$SO_2$—O—, —$SO_2$—NH—, —O—CO—, —CO—NH—$SO_2$—, —$SO_2$—NH—CO—, —O—CO—O— or —O—PO—(OR₂)₂ and $R_2$ is unsubstituted or substituted phenyl, naphthyl or $C_1$–$C_{20}$alkyl, with the proviso, that, if B is not a linking group of formula —O—$SO_2$—, $R_2$ is unsubstituted or substituted phenyl, naphthyl or $C_1$–$C_8$alkyl.

As to $R_1$, $R_2$, X and B the above preferences apply.

Preferably, $R_3$ and $R_4$ are hydrogen, $C_1$–$C_8$alkyl, halogen-substituted $C_1$–$C_8$alkyl, $C_1$–$C_8$alkylsulphonyl or halogen. Preferred alkyl and alkoxy groups $R_3$ and $R_4$ contain 1 to 4 carbon atoms. Highly preferred groups $R_3$ and $R_4$ are hydrogen, $C_1$–$C_4$alkyl or halogen, especially hydrogen.

Of importance are compounds of formula (2), wherein $R_1$ is phenyl which is substituted by $C_1$–$C_4$alkyl, preferably by methyl, X is a group of the formula

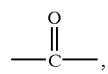

$R_3$ and $R_4$ independently of each other are hydrogen, $C_1$–$C_4$alkyl or halogen, preferably hydrogen, B is a linking group of formula —O—$SO_2$—, and $R_2$ is phenyl which is unsubstituted or substituted by $C_1$–$C_4$alkyl, especially phenyl which is substituted by $C_1$–$C_4$alkyl.

The compounds of formula (2) can be prepared as given above for the compounds of formula (1).

The colour forming compounds are, for example, triphenylmethanes, lactones, benzoxazines, spiropyrans or preferably fluorans.

Preferred colour formers include but are not limited to; 3-diethylamino-6-methylfluoran, 3-dimethylamino-6-methyl-7-anilinofluoran, 3-diethylamino-6-methyl-7-anilinofluoran, 3-diethylamino-6-methyl-7-(2,4-dimethylanilino) fluoran, 3-diethylamino-6-methyl-7-chlorofluoran, 3-diethylamino-6-methyl-7-(3-trifluoromethylanilino) fluoran, 3-diethylamino-6-methyl-7-(2-chloroanilino)fluoran, 3-diethylamino-6-methyl-7-(4-chloroanilino) fluoran, 3-diethylamino-6-methyl-7-(2-fluoroanilino) fluoran, 3-diethylamino-6-methyl-7-(4-n-octylanilino) fluoran, 3-diethylamino-7-(4-n-octylanilino) fluoran, 3-diethylamino -7-(n-octylamino)fluoran, 3-diethylamino-7-(dibenzylamino)fluoran, 3-diethylamino-6-methyl-7-(dibenzylamino) fluoran, 3-diethylamino-6-chloro-7-methylfluoran, 3-diethylamino-7-t-butylfluoran, 3-diethylamino-7-carboxyethylfluoran, 3-diethylamino-6-chloro-7-anilinofluoran, 3-diethylamino-6-methyl-7-(3-methylanilino)fluoran, 3-diethylamino-6-methyl-7-(4-methylanilino)fluoran, 3-diethylamino-6-ethoxyethyl-7-anilinofluoran, 3-diethylamino-7-methylfluoran, 3-diethylamino-7-chlorofluoran, 3-diethylamino-7-(3-trifluoromethylanilino)fluoran, 3-diethylamino-7-(2-chloroanilino)fluoran, 3-diethylamino-7-(2-fluoroanilino) fluoran, 3-diethylamino-benzo[a]fluoran, 3-diethylamino-benzo[c]fluoran, 3-dibutylamino-7-dibenzylaminofluoran, 3-dibutylamino-7-anilinofluoran, 3-diethyiamino-7-anilinofluoran, 3-dibutylamino-6-methylfluoran, 3-dibutylamino-6-methyl-7-anilinofluoran, 3-dibutylamino-6-methyl-7-(2,4-dimethylanilino)fluoran, 3-dibutytamino-6-methyl-7-(2-chloroanilino)fluoran, 3-dibutylamino-6-methyl-7-(4-chloroanilino)fluoran, 3-dibutylamino-6-methyl-7-(2-fluoroanitino)fluoran, 3-dibutylamino-6-methyl-7-(3-trifluoromethylanilino)fluoran, 3-dibutylamino-6-ethoxyethyl-7-anilinofluoran, 3-dibutylamino-6-chloro-anilinofluoran, 3-dibutylamino-6-methyl-7-(4-methylanilino)fluoran, 3-dibutylamino-7-(2-chloroanilino)fluoran, 3-dibutylamino-7-(2-fluoroanilino)

fluoran, 3-dibutylamino-7-(N-methyl-N-formylamino) fluoran, 3-dipentylamino-6-methyl-7-anilinofluoran, 3-dipentylamino-6-methyl-7-(4-2-chloroanilino)fluoran, 3-dipentylamino-7-(3-trifluoromethylanilino)fluoran, 3-dipentylamino-6-chloro-7-anilinofluoran, 3-dipentylamino-7-(4-chloroanilino)fluoran, 3-pyrrolidino-6-methyl-7-anilinofluoran, 3-piperidino-6-methyl-7-anilinofluoran, 3-(N-methyl-N-propylamino)-6-methyl-7-anilinoftuoran, 3-(N-methyl-N-cyclohexylamino)-6-methyl-7-anilinofluoran, 3-(N-ethyl-N-cyclohexylamino)-6-methyl-7-anilinofluoran, 3-(N-ethyl-p-toluidino)-6-methyl-7-anilinofluoran, 3-(N-ethyl-N-isoamylamino)-6-methyl-7-anilinofluoran, 3-(N-ethyl-N-isoamylamino)-6-chloro-7-anilinofluoran, 3-(N-ethyl-N-tetrahydrofurfurylamino)-6-methyl-7-anilinofluoran, 3-(N-ethyl-N-isobutylamino)-6-methyl-7-anilinofluoran, 3-(N-butyl-N-isoamylamino)-6-methyl-7-anilinofluoran, 3-(N-isopropyl-N-3-pentylamino)-6-methyl-7-anilinofluoran, 3-(N-ethyl-N-ethoxypropylamino)-6-methyl-7-anilinofluoran, 3-cyclohexylamino-6-chlorofluoran, 2-methyl-6-p-(p-dimethytaminophenyl)aminoanilinofluoran, 2-methoxy-6-p-(p-dimethylaminophenyl)aminoanilinofluoran, 2-chloro-3-methyl-6-p-(p-phenylaminophenyl)aminoanilinofluoran, 2-diethylamino-6-p-(p-dimethylaminophenyl) aminoanilinofluoran, 2-phenyl-6-methyl-6-p-(p-phenytaminophenyl)aminoanilinofluoran, 2-benzyl-6-p-(p-phenylaminophenyl)aminoanilinofluoran, 3-methyl-6-p-(p-dimethylaminophenyl)amino-anilinofluoran, 3-diethylamino-6-p-(p-diethylaminophenyl) aminoanilinofluoran, 3-diethyl-amino-6-p-(p-dibutylaminophenyl)aminoanilinofluoran, 2,4-dimethyl-6-[(4-dimethylamino)-anilino]fluoran, 3-[(4-dimethylaminophenyl)amino]-5,7-dimethylfluoran, 3,6,6'-tris(dimethyl-amino)spiro[fluorene-9,3'-phthalide], 3,6,6'-tris(diethylamino)spiro[fluorene-9,3'-phthalide], 3,3-bis(p-dimethylaminophenyl)-6-dimethylaminophthalide, 3,3-bis (p-dimethylamino-phenyl)phthalide, 3,3-bis-[2-(p-dimethyiaminophenyl)-2-(p-methoxyphenyl)ethenyl-4,5,6,7-tetrabromophthalide, 3,3-bis-[2-(p-dimethylaminophenyl)-2-(p-methoxyphenyl)ethenyl-4,5,6,7-tetrachlorophthalide, 3,3-bis[1,1-bis(4-pyrrolidinophenyl)ethylene-2-yl]-4,5,6,7-tetrabromophthalide, 3,3-bis-(1-(4-methoxyphenyl)-1-(4-pyrridinophenyl)ethylene-2-yl]-4,5,6,7-tetrachlorophthalide, 3-(4-diethylamino-2-ethoxyphenyl)-3-(1-ethyl-2-methylindole-3-yl)-4-azaphthalide, 3-(4-diethylamino-2-ethoxyphenyl)-3-(1-octyl-2-methylindole-3-yl)-4-azaphthalide, 3-(4-cyclohexylethylamino-2-methoxyphenyl)-3-(1-ethyl-2-methylindole-3-yl)-4-azaphthalide, 3,3-bis(1-ethyl-2-methylindole-3-yl) phthalide, 3,3-bis(1-octyl-2-methylindole-3-yl)phthalide, mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)-4-(4-methoxyphenyl)-8-methyl-7-dimethylamino-3,1-benzoxazine, 4,4'-[1-methylethylidene)-bis(4,1-phenyleneoxy-4,2-quinazolinediyl)]bis[N,N-diethylbenzenamine], bis(N-methyldiphenylamine)-4-yl-(N-butylcarbazole)-3-yl-methane and mixtures thereof.

All of the above colour forming compounds can be used singly or as a mixture with other colour forming compounds; or they may also be used together with further black colour forming compounds.

Highly preferred are 3-diethylamino-6-methyl-7-anilinofluoran, 3-diethylamino-6-methyl-7-(3-methylanilino)fluoran, 3-diethylamino-6-methyl-7-(2,4-dimethylanilino)fluoran, 3-dibutylamino-6-methyl-7-anilinofluoran, 3-dipentylamino-6-methyl-7-anilinofluoran, 3-(N-methyl-N-propylamino)-6-methyl-7-anilinofluoran, 3-(N-methyl-N-cyclohexylamino)-6-methyl-7-anilinofluoran, 3-(N-ethyl-N-isoamylamino)-6-methyl-7-anilinofluoran, 3-diethylamino-6-chloro-7-anilinofluoran, 3-dibutylamino-7-(2-chloroanilino)fluoran, 3-N-ethyl-p-toluidino-6-methyl-7-anilinofluoran, 3-(N-ethyl-N-tetrahydrofurfurylamino)-6-methyl-7-anilinofluoran, 3-(N-ethyl-N-isobutylamino)-6-methyl-7-anilinofluoran, 3-N-ethyl-N-ethoxypropylamino-6-methyl-7-anilinofluoran, 2,4-dimethyl-6-[(4-dimethylamino)anilino]fluoran, 3-(4-diethylamino-2-ethoxyphenyl)-3-(1-octyl-2-methylindole-3yl)-4-azaphthalide, 3,3-bis(pdimethylamino-phenyl)-6-dimethytaminophthalide and mixtures thereof.

It is also possible to use solid solutions comprising at least two colour forming compounds.

A monophase (or single-phase or guest-host) solid solution possesses a crystal lattice which is identical with the crystal lattice of one of its components. One component is embedded as the 'guest' in the crystal lattice of the other component, which acts as the 'host'. The X-ray diffraction pattern of such a monophase solid solution is substantially identical to that of one of the components, called the 'host'. Within certain limits, different proportions of the components produce almost identical results.

In the literature, the definitions by the various authors, such as, G. H. Van't Hoff, A. I. Kitaigorodsky and A. Whitacker for solid solutions and mixed crystals are often contradictory, (cf, e.g. 'Analytical Chemistry of Synthetic Dyes', Chapter 10/page 269, Editor K. Venkataraman, J. Wiley, New York, 1977).

The term 'monophase solid solution' or 'multiphase solid solution' or mixed crystal', as defined herein, therefore, should be taken from the following definitions, which have been adapted to the current improved state of knowledge of such systems:

A monophase (or single-phase or guest-host) solid solution possesses a crystal lattice which is identical with the crystal lattice of one of its components. One component is embedded as the 'guest' in the crystal lattice of the other component, which acts as the 'host'. The X-ray diffraction pattern of such a monophase solid solution is substantially identical to that of one of the components, called the 'host'. Within certain limits, different proportions of the components produce almost identical results.

A multiphase solid solution possesses no precise, uniform crystal lattice. It differs from a physical mixture of its components in that the crystal lattice of at least one of its components is partially or competely altered. In comparison to a physical mixture of the components, which gives an X-ray diffraction diagram that is additive of the diagrams seen for the individual components. The signals in the X-ray diffraction diagram of a multiphase solid solution are broadened, shifted or altered in intensity. In general, different proportions of the components produce different results.

A mixed crystal (or solid compound type) solid solution possesses a precise composition and a uniform crystal lattice, which is different from the crystal lattices of all its components. If different proportions of the components lead, within certain limits, to the same result, then a solid solution is present in which the mixed crystal acts as a host.

For the avoidance of doubt it may also be pointed out that, inter alia, there may also be amorphous structures and mixed aggregates consisting of different particles of different physical type, such as, for example, an aggregate of different components each in pure crystal modification. Such amorphous structures and mixed aggregates cannot be equated with either solid solutions or mixed crystals, and possess different fundamental properties.

As hereinbefore detailed, the monophase solid solutions comprise a plurality of colour compounds. Suitable colour forming materials which may be included in the solid solutions are those given above.

Of particular interest are the following monophase solid solutions:

3-dibutylamino-6-methyl-7-anilinofluoran and 3-dibutylamino-7-dibenzylaminofluoran;

3-dibutylamino-6-methyl-7-anilinofluoran and 3-dibutylamino-7-anilinofluoran;

3-dibutylamino-6-methyl-7-anilinofluoran and 3-diethylamino-7-anilinofluoran;

3-diethylamino-6-methyl-7-anilinofluoran and 3-diethylamino-7-anilinofluoran;

3-dibutylamino-6-methyl-7-anilinofluoran and 3-diethylamino-6-methyl-7-anilinofluoran;

3-dibutylamino-6-methyl-7-anilinofluoran and 3-N-isoamyl-N-ethylamino-6-methyl-7-anilinofluoran;

3-dibutylamino-6-methyl-7-anilinofluoran and 3-N-2-pentyl-N-ethylamino-6-methyl-7-anilinofluoran;

3-dibutylamino-6-methyl-7-anilinofluoran and 3-N-isopropyl-N-ethylamino-6-methyl-7-anilinofluoran;

3-dibutylamino-6-methyl-7-anilinofluoran and 3-N-Cyclohexylmethyl-N-ethylamino-6-methyl-7-anilinofluoran;

3-dibutylamino-6-methyl-7-anilinofluoran and 3-dipropylamino-6-methyl-7-anilinofluoran;

3-dibutylamino-6-methyl-7-anilinofluoran and 3-N-2-butyl-N-ethylamino-6-methyl-7-anilinofluoran;

3-dibutylamino-6-methyl-7-anilinofluoran and 3-N-cyclohexyl-N-methylamino-6-methyl-7-anilinofluoran;

3-dibutylamino-6-methyl-7-anilinofluoran and 3-diethylamino-6-methyl-7-(3-methylanilino) fluoran;

3-dibutylamino-6-methyl-7-anilinofluoran and 3-diethylamino-6-methyl-7-(2,4-dimethylanilino) fluoran;

3-dibutylamino-6-methyl-7-anilinofluoran and 3-dipentylamino-6-methyl-7-anilinofluoran;

3-dibutylamino-6-methyl-7-anilinofluoran and 3-(N-methyl-N-propylamino)-6-methyl-7-anilinofluoran;

3-dibutylamino-6-methyl-7-anilinofluoran and 3-diethylamino-6-chloro-7-anilinofluoran;

3-dibutylamino-6-methyl-7-anilinofluoran and 3-dibutylamino-7-(2-chloroanilinofluoran;

3-dibutylamino-6-methyl-7-anilinofluoran and 3-N-ethyl-p-toluidino-6-methyl-7-anilinofluoran;

3-dibutylamino-6-methyl-7-anilinofluoran and 3-(N-ethyl-N-tetrahydrofurfurylamino)-6-methyl-7-anilinofluoran;

3-dibutylamino-6-methyl-7-anilinofluoran and 3-(N-ethyl-N-isobutylamino)-6-methyl-7-anilinofluoran;

3-dibutylamino-6-methyl-7-anifinofluoran and 3-N-ethyl-N-ethoxypropylamino-6-methyl-7-anilinofluoran;

3-dibutylamino-6-methyl-7-anilinofluoran and 2,4-dimethyl-6-[(4-dimethylamino)anilino]fluoran 3-N-isoamyl-N-ethylamino-6-methyl-7-anilinofluoran and 3-diethylamino-6-methyl-7-anilinofluoran;

3-diethylamino-6-methyl-7-anilinofluoran and 3-N-propyl-N-methylamino-6-methyl-7-anifinofluoran;

3-diethylamino-6-methyl-7-(3-tolyl)aminofluoran and 3-diethylamino-6-methyl-7-anilinofluoran;

3-dibutylamino-6-methyl-7-anilinofluoran and 3,3-bis(1-octyl-2-methylindol-3-yl)phthalide;

3-dibutylamino-6-methyl-7-anilinofluoran and mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)-4-(4-methoxyphenyl)-8-methyl-7-dimethylamino-3,1-benzoxazine;

3-dibutylamino-6-methyl-7-anilinofluoran and 4,4'-[1-methylethylidene)bis(4,1-phenyleneoxy-4,2-quinazolinediyl)]bis[N,N-diethylbenzenamine].

In the above monophase solid solutions the first compound is in a molar ratio of 75 to 99.9% by mole, the second compound is in a ratio of 25 to 0.1% by mole.

Examples of monophase solid solutions comprising two components A and B in the stated ratios are: 3-dibutylamino-6-methyl-7-anilinofluoran (99.9%), 3-diethylamino-6-methyl-7-anilinofluoran (0.1%);

3-dibutylamino-6-methyl-7-anilinofluoran (99%), 3-diethylamino-6-methyl-7-anilinofluoran (1%);

3-dibutylamino-6-methyl-7-anilinofluoran (95%), 3-diethylamino-6-methyl-7-anilinofluoran (5%);

3-dibutylamino-6-methyl-7-anilinofluoran (90%) and 3-N-2-pentyl-N-ethylamino-6-methyl-7anilinofluoran (10%);

3-dibutylamino-6-methyl-7-anilinofluoran (95%) and 3-N-2-pentyl-N-ethylamino-6-methyl-7-anilinofluoran (5%);

3-dibutylamino-6-methyl-7-anilinofluoran (90%) and 3-N-isopropyl-N-ethylamino-6-methyl-7-anilinoftuoran (10%);

3-dibutylamino-6-methyl-7-anilinofluoran (95%) and 3-N-isopropyl-N-ethylamino-6-methyl-7-anilinofluoran (5%);

3-dibutylamino-6-methyl-7-anilinofluoran (90%) and 3-N-Cyclohexylmethyl-N-ethylamino-6-methyl-7-anilinofluoran (10%);

3-dibutylamino-6-methyl-7-anilinofluoran (95%) and 3-N-Cyclohexylmethyl-N-ethylamino-6-methyl-7-anilinofluoran (5%);

3-dibutylamino-6-methyl-7-anilinofluoran (90%) and 3-dipropylamino-6-methyl-7-anilinofluoran (10%);

3-dibutylamino-6-enethyl-7-anilinofluoran (95%) and 3-dipropylamino-6-methyl-7-anilinofluoran (5%);

3-dibutylamino-6-methyl-7-anilinofluoran (90%) and 3-N-2-butyl-N-ethylamino-6-methyl-7-anilinofluoran (10%);

3-dibutylamino-6-methyl-7-anilinofluoran (95%) and 3-N-2-butyl-N-ethylamino-6-methyl-7-anilinofluoran (5%);

3-dibutylamino-6-methyl-7-anilinofluoran (90%), 3-diethylamino-6-methyl-7-anilinofluoran (10%);

3-dibutyfamino-6-methyl-7-anilinofluoran (85%), 3-diethyiamino-6-methyl-7-anilinofluoran (15%);

3-dibutylamino-6-methyl-7-anilinofluoran (80%), 3-diethylamino-6-methyl-7-anilinofluoran (20%);

3-dibutylamino-6-methyl-7-anifinofluoran (95%), 3-N-isoamyl-N-ethylamino-6-methyl-7-anilinofluoran (5%);

3-dibutylamino-6-methyl-7-anilinofluoran (90%), 3-N-isoamyl-N-ethylamino-6-methyl-7-anilinofluoran (10%);

3-dibutylamino-6-methyl-7-anilinofluoran (80%), 3-N-isoamyl-N-ethylamino-6-methyl-7-anilinofluoran (20%);

3-dibutylamino-6-methyl-7-anilinofluoran (90%), 3-N-cyclohexyl-N-methylamino-6-methyl-7-anilinofluoran (10%);

3-diethylamino-6-methyl-7-anilinofluoran (90%), 3-N-isoamyl-N-ethylamino-6-methyl-7-anilinofluoran (10%);

3-diethylamino-6-methyl-7-anilinofluoran (80%), 3-N-isoamyl-N-ethylamino-6-methyl-7-anilinofluoran (20%);

3-diethylamino-6-methyl-7-anilinofluoran (20%), 3-N-isoamyl-N-ethylamino-6-methyl-7-anifinofluoran (80%);

3-diethylamino-6-methyl-7-anilinofluoran (10%), 3-N-isoamyl-N-ethylamino-6-methyl-7-anilinofluoran (90%);

3-diethyiamino-6-methyl-7-anilinofluoran (90%), 3-N-propyl-N-methylamino-6-methyl-7-anilinofluoran (10%);

3-diethylamino-6-methyl-7-anilinofluoran (80%), 3-N-propyl-N-methylamino-6-methyl-7-anilinofluoran (20%);

3-diethylamino-6-methyl-7-anilinofluoran (20%), 3-N-propyl-N-methylamino-6-methyl-7-anilinofluoran (80%);

3-diethylamino-6-methyl-7-anilinofluoran (10%), 3-N-propyl-N-methylamino-6-methyl-7-anilinofluoran (90%);

3-diethylamino-6-methyl-7-anilinofluoran (10%), 3-diethylamino-6-methyl-7-(3-tolyl)aminofluoran (90%);

3-diethylamino-6-methyl-7-anilinofluoran (20%), 3-diethylamino-6-methyl-7-(3-tolyl)aminofluoran (80%);

3-dibutylamino-6-methyl-7-anilinofluoran (90%), 3,3-bis(1-octyl-2-methylindol-3-yl)phthalide (10%);

3-diethyiamino-6-methyl-7-anilinofluoran (80%), 3,3-bis(1-octyl-2-methylindol-3-yl)phthalide(20%);

3-dibutylamino-6-methyl-7-anilinofluoran (90%), mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)4-(4-methoxyphenyl)-8-methyl-7-dimethylamino-3,1-benzoxazine(10%);

3-dibutylamino-6-methyl-7-anifinofluoran (80%), mixture of 2-phenyl-4-(4-diethylaminophenyl)-4-(4-methoxyphenyl)-6-methyl-7-dimethylamino-3,1-benzoxazine and 2-phenyl-4-(4-diethylaminophenyl)-4-(4-methoxyphenyl)-8-methyl-7dimethylamino-3,1-benzoxazine(20%);

3-dibutylamino-6-methyl-7-anilinofluoran (90%), 4,4'-[1-methylethylidene)bis(4,1-phenyleneoxy-4,2-quinazolinediyl)bis(N,N-diethylbenzenamine](10%);

3-dibutylamino-6-methyl-7-anilinofluoran (80%), 4,4'-[1-methylethylidene)bis(4,1-phenyleneoxy-4,2-quinazolinediyl)]bis[N,N-diethylbenzenamine] (20%).

The monophase solid solutions can be used singly or as a mixture with other colour forming compounds such as triphenylmethanes, lactones, fluorans, benzoxazines and spiropyrans; or they may also be used together with further black colour forming compounds. Examples of such other colour forming compounds are given hereinbefore.

The monophase solid solutions can be prepared by a variety of methods. One such method is the recrystallisation method wherein a physical mixture of the desired components is dissolved, with or without heating, in a suitable solvent or solvent mixture. Suitable solvents include but are not limited to toluene, benzene, xylene, dichlorobenzene, chlorobenzene, 1,2-dichloroethane, methanol, ethanol, iso-propanol, n-butanol, acetonitrile, dimethylformamide or mixtures of these solvents with each other and with water. The monophase solid solution is then isolated by crystallisation from the solvent or solvent mixture. This can be brought about by cooling, standing, addition of a further solvent to promote crystallisation or concentration by standard means such as distillation, steam distillation and vacuum distillation. When the monophase solid solution is isolated by concentration it may be advantageous to do so in the presence of a small amount of base, to improve the visual aspect of the isolated product.

Alternatively, monophase solid solutions can be prepared from mixtures of the appropriate starting materials. The technique can be used to produce mixtures of two or more fluorans or phthalides. For example, mixtures of two fluorans are produced by replacing a single starting material with two analogous materials to the same total molar concentration in the reaction. In the case of fluorans, these starting materials are derivatives of amino phenols, phthalic anhydrides, keto acids and diphenylamines.

In addition, the heat sensitive recording material can contain a previously known developer, unless the colour forming performance of the resultant heat sensitive material is disturbed thereby. Such developers are exemplifed by but not limited to; 4,4'-isopropylidene bisphenol, 4,4'-sec-butylidene bisphenol, 4,4'-cyclohexylidene bisphenol, 2,2-bis-(4-hydroxyphenyl)-4-methylpentane, 2,2-dimethyl-3,3-di(4-hydroxyphenyl)butane, 2,2'-dihydroxydiphenyl, 1-phenyl-1,1-bis(4-hydroxyphenyl)butane, 4-phenyl-2,2-bis(4-hydroxyphenyl)butane, 1-phenyl-2,2-bis(4-hydroxyphenyl)butane, 2,2-bis(4'-hydroxy-3'-methylphenyl)-4-methylpentane, 2,2-bis(4'-hydroxy-3'-tert-butyllphenyl)-4-methylpentane, 4,4'-sec-butylidene-bis(2-methylphenol), 4,4'-isopropylidene-bis (2-tert-butylphenol), 2,2-bis(4'-hydroxy-3'-isopropylphenyl)-4-methylpentane, allyl-4,4-bis (4'-hydroxyphenyl) pentanoate, propargyl-4,4-bis(4'-hydroxyphenyl)pentanoate, n-propyl-4,4-bis (4'-hydroxyphenyl)pentanoate, 2,4-bis (phenylsulfonyl)phenol, 2-(4-methylsulfonyl)-4-(phenylsulfonyl)phenol, 2-(phenylsulfonyl)-4-(4-methylsulfonyl)phenol, 2,4-bis (4-methylphenylsulfonyl) phenol, pentamethylene-bis(4-hydroxybenzoate), 2,2-dimethyl-3,3-di(4-hydroxyphenyl)pentane, 2,2-di(4-hydroxyphenyl)hexane, 4,4'-dihydroxydiphenyl thioether, 1,7-di(4-hydroxyphenylthio)-3,5-dioxaheptane, 2,2'-bis(4-hydroxyphenylthio)diethyl ether, 4,4'-dihydroxy-3,3'-dimethylphenyl thioether; benzyl-4-hydroxybenzoate, ethyl-4-hydroxybenzoate, propyl-4-hydroxybenzoate, isopropyl-4-hydroxybenzoate, butyl-4-hydroxybenzoate, isobutyl-4-hydroxybenzoate, 4,4'-dihydroxydiphenylsulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone, 4,4'-dihydroxy-3,3',5,5'-tetrabromodiphenyl sulfone, 4,4'-bis (p-toluenesulphonylaminocarbonylamino) diphenyimethane, N-p-toluenesulphonyl-N'-phenyl urea, dimethyl 4-hydroxyphthalate, dicyclohexyl 4-hydroxyphthalate, diphenyl 4-hydroxyphthalate, 4-[2-(4-methoxyphenyloxy)ethyloxy] salicylate, 3,5-di-tert-butylsalicylic acid, 3-benzyl salicylic acid, 3-(α-methylbenzyl) salicylic acid, 3-phenyl-5-(α,α- dimethylbenzyl) salicylic acid, 3,5-di-α-methylbenzyl salicylic acid; metal salts of salicylic acid, 2-benzylsulfonylbenzoic acid, 3-cyclohexyl-4-hydroxybenzoic acid, zinc benzoate, zinc 4-nitrobenzoate, 4-(4'-phenoxybutoxy)phthalic acid, 4-(2'-phenoxyethoxy) phthalic acid, 4-(3'-phenylpropyloxyyphthalic acid, mono (2-hydroxyethyl)-5-nitro-isophthalic acid, 5-benzyloxycarbonyl isophthalic acid, 5-(1'-phenylethanesulfonyl)isophthalic acid, bis(1,2-dihydro-1,5-dimethyl-2-phenyl-3H-pyrazol-3-one-O)bis(thiocyanato-N) zinc and mixtures thereof.

In addition, the heat sensitive recording material of the invention can contain a sensitiser.

Representative examples of sensitiser are stearamide, methylol stearamide, p-benzylbiphenyl, m-terphenyl, 2-benzyloxynaphthalene, 4-methoxybiphenyl, dibenzyl oxalate, di(4-methylbenzyl)oxalate, di(4-chlorobenzyl) oxalate, dimethyl phthalate, dibenzyl terephthalate, dibenzyl isophthalate, 1,2-diphenoxyethane, 1,2-bis(4-methylphenoxy)ethane, 1,2-bis(3-methylphenoxy)ethane, 4,4'-dimethylbiphenyl, phenyl-1-hydroxy-2-naphthoate, 4-methylphenyl biphenyl ether, 1,2-bis(3,4-dimethylphenyl) ethane, 2,3,5,6-4'-methyldiphenyl methane, 1,4-diethoxynaphthalene, 1,4-diacetoxybenzene, 1,4-diproprionoxybenzene, o-xylylene-bis(phenyl ether), 4-(m-methylphenoxymethyl) biphenyl, p-hydroxyacetanilide, p-hydroxybutyranilide, p-hydroxynonananilide, p-hydroxylauranilide, p-hydroxyoctadecan-anilide, N-phenyl-phenylsulphonamide and sensitisers of the formula

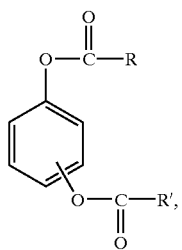

(3)

wherein R and R' are identical or different from each other and each represent $C_1$–$C_6$alkyl.

Examples of R and R' are methyl, ethyl, n- or iso-propyl and n-, sec- or tert-butyl.

The substituents R and R' are identical or different from each other and each are preferably $C_1$–$C_4$alkyl, especially methyl or ethyl, in particular ethyl.

The above sensitisers are known or can be prepared according to known methods.

In addition, the heat sensitive recording material of the invention can contain a stabiliser.

Representative stabilisers for use in heat sensitive recording materials include 2,2'-methylene-bis(4-methyl-6-tert-butylphenol), 2,2'-methylene-bis(4-ethyl-6-tert-butylphenol), 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl) butane, 1,1,3-tris(2-methyl-4-hydroxy-5-cyclohexylphenyl)butane, bis (3-tert-butyl-4-hydroxy-6-methylphenyl)sulfone, bis (3,5-dibromo-4-hydroxyphenyl)sulfone, 4,4'-sulfinyl bis (2-tert-butyl-5-methylphenol), 2,2'-methylene bis (4,6-di-tert-butylphenyl)phosphate and alkali metal, ammonium and polyvalent metal salts thereof, 4-benzyloxy-4'-(2-methylglycidyloxy)diphenyl sulfone, 4,4'-diglycidyloxydiphenyl sulfone,1,4-diglycidyloxybenzene, 4-[a-(hydroxymethyl)benzyloxy]4-hydroxydiphenyl sulfone, metal salts of p-nitrobenzoic acid, metal salts of phthalic acid mono benzyl ester, metal salts of cinnamic acid and mixtures thereof.

Preferred stabilisers are 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl)butane, 4-benzyloxy-4'-(2-methylglycidyloxy)diphenyl sulfone and mixtures thereof.

The heat sensitive recording material of the invention can be prepared according to conventional methods. For example, at least one colour forming compound, at least one developer and, if desired, at least one sensitiser are pulverised separately in water or a suitable dispersing medium, such as aqueous polyvinyl alcohol, to form an aqueous or other dispersion. If desired a stabiliser is treated in the same manner. The fine particle dispersions thus obtained are combined and then mixed with conventional amounts of binder, filler and lubricant.

Representative binders used for the heat sensitive recording material include polyvinyl alcohol (fully and partially hydroiysed), carboxy, amide, sulfonic and butyral modified polyvinyl alcohols, derivatives of cellulose such as hydroxyethyl cellulose, methyl cellulose, ethyl cellulose, carboxymethyl cellulose and acetyl cellulose, copolymer of styrene-maleic anhydride, copolymer of styrene-butadiene, polyvinyl chloride, polyvinyl acetate, polyacrylamide, polyamide resin and mixtures thereof.

Exemplary fillers which can be used include calcium carbonate, kaolin, calcined kaolin, aluminium hydroxide, talc, titanium dioxide, zinc oxide, silica, polystyrene resin, urea-formaldehyde resin, hollow plastic pigment and mixtures thereof.

Representative lubricants for use in heat sensitive recording materials include dispersions or emulsions of stearamide, methylene bisstearamide, polyethylene, carnauba wax, paraffin wax, zinc stearate or calcium stearate and mixtures thereof.

Other additives can also be employed, if necessary. Such additives are for example fluorescent whitening agents and ultraviolet absorbers.

The coating composition so obtained can be applied to a suitable substrate such as paper, plastic sheet and resin coated paper, and used as the heat sensitive recording material. The system of the invention can be employed for other end use applications using colour forming materials, for example, a temperature indicating material.

The quantity of the coating is usually in the range of 2 to 10 g/m$^2$, most often in the range 4 to 8 g/m$^2$.

The recording material containing such a thermosensitive colouring layer can in addition contain a protective layer and, if desired, an undercoat layer. The undercoat layer may be interposed between the substrate and the thermosensitive colouring layer.

The protective layer usually comprises a water-soluble resin in order to protect the thermosensitive colouring layer. If desired, the protective layer may contain water-soluble resins in combination with water-insoluble resins.

As such resins conventional resins can be employed. Specific examples are: polyvinyl alcohol; starch and starch derivatives; cellulose derivatives such as methoxycellulose, hydroxyethylcellulose, carboxymethylcellulose, methylcellulose and ethylcellulose; sodium polyacrylate; polyvinyl pyrrolidone; polyacrylamide/acrylic acid ester copolymers; acrylamide/acrylic acid ester/methacrylic acid copolymers; alkali metal salts of styrene/maleic anhydride copolymers;

alkali metal salts of isobutylene/maleic anhydride copolymers; polyacrylamide; sodium alginate; gelatin; casein; water-soluble polyesters and carboxyl-group-modified polyvinyl alcohols.

The protective layer may also contain a water-resisting agent such as a polyamide resin, melamine resin, formaldehyde, glyoxal or chromium alum.

Furthermore, the protective layer may contain fillers, such as finely-divided inorganic powders, e.g. of calcium carbonate, silica, zinc oxide, titanium oxide, aluminium hydroxide, zinc hydroxide, barium sulphate, clay, talc, surface-treated calcium or silica, or a finely-divided organic powder of, e.g., a urea-formaldehyde resin, a styrene/methacrylic acid copolymer or polystyrene.

The undercoat layer usually contains as its main components a binder resin and a filler.

Specific examples of binder resins for use in the undercoat layer are: polyvinyl alcohol; starch and starch derivatives; cellulose derivatives such as methoxycellulose, hydroxyethylcellulose, carboxymethylcellulose, methylcellulose and ethylcellulose; sodium polyacrylate; polyvinyl pyrrolidone; polyacrylamide/acrylic acid ester copolymers; acrylamide/acrylic acid ester/methacrylic acid copolymers; alkali metal salts of styrene/maleic anhydride copolymers; alkali metal salts of isobutylene/maleic anhydride copolymers; polyacrylamide; sodium alginate; gelatin; casein; water-soluble polymers such as water-soluble polyesters and carboxyl-group-modified polyvinyl alcohols; polyvinyl acetate; polyurethanes; styrene/butadiene copolymers; polyacrylic acid; polyacrylic acid esters; vinyl chloride/vinyl acetate copolymers; polybutylmethacrylate; ethylen/vinylacetate copolymers and styrene/butadiene acrylic derivative copolymers.

Specific examples of fillers for use in the undercoat layer are: finely-divided inorganic powders, e.g. of calcium carbonate, silica, zinc oxide, titanium oxide, aluminium hydroxide, zinc hydroxide, barium sulphate, clay, talc, surface-treated calcium, silica or calcined clay (eg Ansilex, Engelhard Corp.), and finely-divided organic powders of, e.g., urea-formaldehyde resins, styrene/methacrylic acid copolymers and polystyrene.

In addition, the undercoat layer may contain a water-resisting agent. Examples of such agents are given above.

In particular the invention provides exceptional resistance to plasticiser, oil and heat ageing whilst showing an improved background whiteness.

The following non-limiting examples, illustrate the novel materials of the present invention.

SYNTHESIS EXAMPLE 1

Preparation of N-(p-Toluenesulphonyl)-N'-(3-n-butylaminosulphonylphenyl)urea

To a stirred solution of 4.6 g aminobutylbenzenesulphonamide in 10 g dimethylformamide at room temperature was added 4.14 g toluenesulphonylisocyanate. After three hours at room temperature 0.65 g toluenesulphonylisocyanate was added and stirring continued for one hour. To the reaction mixture was added water and methanol to precipitate the product as a white solid which was isolated by filtration and washed with methanol. After drying in vacuo at 80° C. the product was obtained in 8.1 g yield, melting point 153–153.3° C.

SYNTHESIS EXAMPLE 2

Preparation of N-(p-Toluenesulphonyl)-N'-(4-trimethylacetophenyl)urea

A mixture of 22.3 g 4-nitrophenyltrimethylacetate and 300 g of isopropanol was charged to a Buchi catalytic hydrogenator with 2 g 5%Pd-C. The mixture was then hydrogenated at 60° C. and 10bar until hydrogen uptake ceased. The reaction mixture was cooled, filtered and the solvent removed to yield 18.7 g of 4-aminophenyltrimethylacetate as a white solid, melting point 56.2–56.5° C.

The 4-aminophenyltrimethylacetate 15.4 g, was then converted to the product using the method described in Example 1 to give 27 g of a white solid which was isolated by filtration and washed with isopropanol, melting point 177.8–178.30° C.

SYNTHESIS EXAMPLE 3

Preparation of N-(Benzenesulphonyl)-N'-(3-p-toluenesulphonyloxyphenyl)urea

To a stirred solution of 5.65 g m-aminophenol in 45m-acetonitrile was added dropwise 9.5 g benzenesulphonylisocyanate such that the temperature was maintained at <40° C. The mixture was stirred for one hour at room temperature and allowed to stand overnight. To the reaction was then added 25ml water and 5.35 g 47% caustic soda and the reaction was heated to 55–60° C. To this was added, over two hours, 9.93 g p-toluenesulphonylchloride with simultaneous addition of 47% caustic soda so as to maintain the pH between 10 and 11. After two hours at 60° C. the reaction mass was neutralised with hydrochloric acid to produce a thick white precipitate of the desired product. This was isolated by filtration and washed with water to give after drying 21.1 g of product, melting point 162–170° C.

SYNTHESIS EXAMPLE 4

Preparation of N-(p-Toluenesulphonyl)-N'-(3-p-toluenesulphonyloxyphenyl)urea

To a solution of 81.75 g m-aminophenol in 77.4 g 47% caustic soda and 44.3 g water at 65° C. was added, dropwise over three hours, 143.7 g p-toluenesulphonylchloride. The m-toluenesulphonyloxyaniline precipitated during the course of the addition was isolated by filtration and washed alkaline free with water to give 101.4 g of solid.

The m-toluenesulphonyloxyaniline was then converted to the product using the method described in Example 1 to give a white solid with melting point 155–159° C.

SYNTHESIS EXAMPLE 5

Preparation of N-(p-Toluenesulphonyl)-N'-(3-phenylsulphonyloxyphenyl)urea

A stirred solution of N-toluenesulphonylethylcarbamate (1.21 g), 3-phenylsulphonyloxyaniline (1.24 g) and triethylamine (0.55 g) in acetonitrile (25ml) was heated under reflux for 22 hours. The reaction mass was allowed to cool and diluted with water to precipitate the product as a white solid.

SYNTHESIS EXAMPLES 5a to 44

According to the above synthetic methods the N,N' disubstituted ureas given in the following Table 1 can be prepared.

TABLE 1

| Synthesis Example | N | N' | Melting Point (° C.) | Synthetic Method according to Example |
|---|---|---|---|---|
| 5a | p-Toluenesulphonyl | 3-Phenylsulphonyloxyphenyl | 149.5–153 | 4 |
| 6 | p-Toluenesulphonyl | 2-p-Toluenesulphonyloxyphenyl | 149.8–152.5 | 4 |
| 7 | p-Toluenesulphonyl | 2-Phenylsulphonyloxyphenyl | 156–160.4 | 4 |
| 8 | p-Toluenesulphonyl | 4-Benzoyloxyphenyl | 229–231 | 2 |
| 9 | p-Toluenesulphonyl | 4-Phenylsulphonyloxyphenyl | 161–163 | 4 |
| 10 | p-Toluenesulphonyl | 4-Acetoxyphenyl | about 200 | 2 |
| 11 | p-Toluenesulphonyl | 2-p-Toluenesulphonyloxy-5-ethylsulphonyl phenyl | 167–169 | 4 |
| 12 | o-Toluenesulphonyl | 3-p-Toluenesulphonyloxyphenyl | 178–183 | 4 |
| 13 | 4-Chlorobenzene sulphonyl | 3-p-Toluenesulphonyloxyphenyl | 144–151 | 4 |
| 14 | p-Toluenesulphonyl | 4-p-Toluenesulphonyloxyphenyl | 190–193 | 2 |
| 15 | p-Toluenesulphonyl | 3-Butylsulphonyloxyphenyl | 158–163 | 3 |
| 16 | p-Toluenesulphonyl | 2-Methyl-4-p-toluenesulphonyloxyphenyl | 176–180 | 4 |
| 17 | p-Toluenesulphonyl | 5-methyl-3-p-toluenesulphonyloxy-2-pyrimidyl | 169–171 | 4 |
| 18 | p-Toluenesulphonyl | 5-p-Toluenesulphonyloxynapthyl | 145–148 | 4 |
| 19 | p-Toluenesulphonyl | 4-p-Tolyloxysulphonylphenyl | 168–169 | 3 |
| 20 | p-Toluenesulphonyl | 3-Octylsulphonyloxyphenyl | | 3 |
| 21 | p-Toluenesulphonyl | 3-Hexadecylsulphonyloxyphenyl | 153–159 | 3 |
| 22 | Octylsulphonyl | 3-p-Toluenesulphonyloxyphenyl | 118–120 | 5 |
| 23 | p-Toluenesulphonyl | 4-Phenylsulphonyloxyphenyl | 161–163 | 4 |
| 24 | Phenylsulphonyl | 3-(p-Toluenesulphonyloxy)phenyl | 149–151.6 | 4 |
| 25 | p-Toluenesulphonyl | 3-Trimethylacetoxyphenyl | | 3 |
| 26 | 4-Chlorophenylsulphonyl | 4-(p-Toluenesulphonyloxy)phenyl | 177.8–179 | 4 |
| 27 | p-Toluenesulphonyl | 4-Acetophenyl | 184.5–185.5 | 1 |
| 28 | p-Toluenesulphonyl | 4-Acetamidosulphonylphenyl | 192.8–193.2 | 1 |
| 29 | p-Toluenesulphonyl | 3-(Ethoxycarbonyloxy)phenyl | 186.8–188 | 3 |
| 30 | p-Toluenesulphonyl | 3-(Ethoxycarbamyl)phenyl | 139.8–141 | 2 |
| 31 | p-Toluenesulphonyl | 3-(2-napthylsulphonyloxy)phenyl | 151.2–152 | 3 |
| 32 | p-Toluenesulphonyl | 4-Benzoylphenyl | 185–187 | 1 |
| 33 | p-Toluenesulphonyl | 3-(4-toluenesulphonylamino)phenyl | 193.5–195.3 | 2 |
| 34 | p-Toluenesulphonyl | 3-Acetaminophenyl | 192.8–193.7 | 2 |
| 35 | 4-Chlorophenylsulphonyl | 4-Trimethylacetamidophenyl | 187–189.4 | 2 |
| 36 | Benzenesulphonyl | 4-Trimethyl acetamidophenyl | 159–167 | 2 |
| 37 | 4-Chlorophenylsulphonyl | 2-(p-Toluenesulphonyloxy)phenyl | 161–164 | 4 |
| 38 | p-Toluenesulphonyl | 3-(N,N-di-p-Toluene-sulphonyl)aminophenyl | 162.5–165 | 1 |
| 39 | Benzenesulphonyl | 2-(p-Toluenesulphonyloxy)phenyl | 157–160 | 4 |
| 40 | 4-Chlorophenylsulphonyl | 4-Acetamidosulphonylphenyl | 187–188 | 1 |
| 41 | p-Toluenesulphonyl | 3-(Diphenylphosphinyl)phenyl | 140–141.5 | 3 |
| 42 | p-Toluenesulphonyl | 4-Benzyloxyphenyl | 154–155.3 | 1 |
| 43 | p-Toluenesulphonyl | 3-Benzyloxyphenyl | 153.9–155.3 | 1 |
| 44 | p-Toluenesulphonyl | 3-Phenyloxyphenyl | 166.5–168.5 | 1 |

SYNTHESIS EXAMPLE 45

Preparation of a Monophase Solid Solution From 2'-carboxy-4-diethyiamino-2-hydroxybenzophenone (90 mol%) and 2'-carboxy-4-diethylamino-2-hydroxybenzophenone (10 mol%)

To 249.5 g of 98% sulphuric acid and 61.2 g oleum was added, 78.97 g of 2'-carboxy-4-dibutylamino-2-hydroxybenzophenone and 7.44 g of 2'-carboxy-4-diethylamino-2-hydroxybenzophenone over about 2hr with the temperature being maintained below about 25° C. by use of an ice-bath. Once in solution, 50.7 g of 4-methoxy-2-methyidiphenylamine was added and the mixture was stirred for about 3hr at 30° C. The reaction mass was then added, over about 30 minutes with stirring, to a mixture of 135 g toluene-45 g water at 85° C. To this was then added, over 30 minutes, 135.7 g water. Agitation was ceased and the separated aqueous phase was removed. To the remaining organic phase was added 244 g sodium hydroxide 100°TW, 199 g toluene and 387 g water and the reaction was stirred for 2h at 85° C. The reaction was cooled to 25° C. and the precipitated product was isolated by filtration. The product was washed with hot water (about 60° C.) then methanol and dried to yield 106.2 g of a monophase solid solution (melting point 179.9–181.4° C).

EXAMPLE 1

Preparation of Heat Sensitive Coating Formulations Containing N-(p-toluenesulphonyl)-N'-(3-p-Toluenesulphonyloxyphenyl)urea Dispersions A to C were prepared by grinding the compositions shown below in an attritor until an average particle size of 1–1.5 $\mu$ was attained.

| Dispersion A (Colour Former) | |
|---|---|
| 3-dibutylamino-6-methyl-7-anilinofluoran | 3.01 parts |
| Polyvinyl alcohol (10% aqueous solution) | 10.50 parts |
| Water | 6.49 parts |
| Dispersion B (Colour Developer) | |
| N-(p-toluenesulphonyl)-N'-(3-p-toluenesulphonyloxyphenyl) urea | 7.5 parts |
| Polyvinyl alcohol (10% aqueous solution) | 7.5 parts |
| Water | 22.5 parts |
| Dispersion C (Sensitiser) | |
| parabenzylbiphenyl | 10.0 parts |
| Polyvinyl alcohol (10% aqueous solution) | 10.0 parts |
| Water | 20.0 parts |

A thermal coating mixture was then prepared by combining together the following components:

|  | parts by weight |
| --- | --- |
| Dispersion A | 6.6 |
| Dispersion B | 10.0 |
| Dispersion C | 6.0 |
| Calcium Carbonate (25% aqueous dispersion) | 12.0 |
| Zinc stearate (33% aqueous dispersion) | 0.9 |
| Polyvinyl alcohol (10% aqueous solution) | 4.5 |
| Tinopal ® ABP-X (fluorescent whitening agent) | 0.12 |
| Water | 2.48 |

This coating mixture was applied on one side of a base paper weighing 50 g/m² in a coating weight of about 5.0 g/m² and then dried. The resulting sheet was calendered by means of a laboratory calender to produce a recording sheet with excellent background whiteness.

The heat sensitive recording paper obtained demonstrates excellent background whiteness of paper after application of the coating liquid and in storage stability, i.e. resistance to light, heat and moisture, of uncoloured portion of the coated paper and excellent resistance of the image to cottonseed oil, plasticiser, heat, heat and moisture, water. Additionally, the recording paper obtained shows a high dynamic sensitivity.

DESCRIPTION OF TEST METHODS

Background Whiteness Before and After Ageing:

This test assesses the effects of heat and moisture on unprinted thermal paper.

The whiteness of unprinted paper is measured using a Macbeth 1200 series Densitometer, before and after ageing for one hour at 60° C. and 50% R.H.

Dynamic Sensitivity at Various Pulse Widths:

This test assesses the sensitivity and intensity of the image produced on thermal paper.

Ten individual print areas are printed with increased amounts of energy using an Atlantek thermal response tester model 200. The optical density of each image is measured using a Macbeth 1200 series Densitometer.

Lightfastness Tests (120 Hours Exposure):

This test assesses the stability of the thermal paper, including the image, after exposure to sunlight.

An image is produced using an Atlantek thermal response tester model 200. The image including background is placed at a distance of 8 cm below 40W fluorescent tubes emitting artificial sunlight (approximately 1200 Lux) for 120 hours. The optical density of the image and background whiteness of the paper are measured before and after exposure with a Macbeth 1200 series Densitometer.

Cottonseed Oil Resistance of Image:

This test assesses the stability of the image when exposed to cottonseed oil.

An image is produced using an Atlantek thermal response tester model 200. Cottonseed oil is then Gravure printed onto the image which is then stored at 40° C. for 24 hours. The optical density of the image is measured using a Macbeth 1200 series Densitometer before and after exposure.

Plasticiser Resistance of Image and Background:

This test assesses the stability of the image and background when exposed to PVC containing 20–25% phthalate ester-type plasticiser.

An image is produced using an Atlantek thermal response tester model 200. The image is put into contact with the PVC under 107 g cm$^{-2}$ pressure for 24 hours at 50° C. The optical density of the image and background are measured using a Macbeth 1200 series Densitometer before and after exposure.

Waterfastness of Image:

This test assesses the stability of the image after immersion in water.

An image is produced using an Atlantek thermal response tester model 200. The image is immersed in de-ionised water at room temperature for 24 hours. The optical density of the image is measured using a Macbeth 1200 series Densitometer before and after immersion.

Heat and Moisture Resistance of Image:

This test assesses the effects of heat and moisture on the image.

An image is produced using an Atlantek thermal response tester model 200. The image is aged at 60° C. at 70% R.H. for 24 hours. The optical density of the image is measured using a Macbeth 1200 series Densitometer before and after exposure.

Heat Resistance of Image and Background at 80° C.:

This test assesses the effect of heat on both the image and background of thermal paper.

An image is produced using an Atlantek thermal response tester model 200. The image is aged at 80° C. for 24 hours. The optical density of the image and background are measured using a Macbeth 1200 series Densitometer before and after exposure.

Static Sensitiviay and Background Storage Stabilioy

This test determines the the r mal sensitivity of thermal paper.

Thermal paper is exposed to a range of temperatures for a fixed period of 1 second. Twelve separately heated blocks at 50°, 60°, 70°, 75°, 80°, 85°, 90°, 95°, 100°, 110°, 120° and 150° C. are applied to the paper to produce an image. The optical density of each image is measured using a Macbeth 1200 series Densitometer.

From the static sensitivity, the temperature at which a density of 0.2 occurs is calculated This temperature gives an indication of the background storage stability of the paper.

EXAMPLES 2 to 48

The following Table 2 shows the colour former/developer/sensitiser combinations that were used in each example. The heat sensitive recording material was prepared by the method described in example 1. In all cases, the heat sensitive recording paper thus obtained demonstrates excellent background whiteness of paper after application of the coating liquid and in storage stability, i.e. resistance to light, heat and moisture, of uncoloured portion of the coated paper and excellent resistance of the image to cottonseed oil, plasticiser, heat, heat and moisture, water.

TABLE 2

| Example | Colour Former | Sensitiser | Developer |
| --- | --- | --- | --- |
| 2 | 3-dibutylamino-6-methyl-7-anilinofluoran | parabenzylbiphenyl | Synthesis Example 4 |
| 3 | 3-diethylamino-6-methyl-7-anilinofluoran | parabenzylbiphenyl | Synthesis Example 4 |
| 4 | 3-(N-ethyl-N-isoamylamino)-6-methyl-7-anilinofluoran | parabenzylbiphenyl | Synthesis Example 4 |

TABLE 2-continued

| Example | Colour Former | Sensitiser | Developer |
|---|---|---|---|
| 5 | 3-(N-cyclohexyl-N-methylamino)-6-methyl-7-anilinofluoran | parabenzylbiphenyl | Synthesis Example 4 |
| 6 | 3-( N-propyl-N-methylamino)-6-methyl-7-anilinofluoran | parabenzylbiphenyl | Synthesis Example 4 |
| 7 | monophase solid solution of 3-dibutylamino-6-methyl-7-anilinofluoran (9 parts) and 3-diethylamino-6-methyl-7-anilinofluoran (1 part) | parabenzylbiphenyl | Synthesis Example 4 |
| 8 | 3-dibutylamino-6-methyl-7-anilinofluoran | 2-Benzyloxy naphthalene | Synthesis Example 4 |
| 9 | 3-dibutylamino-6-methyl-7-anilinofluoran | Ethyleneglycolbis-m-tolylether. | Synthesis Example 4 |
| 10 | 3-dibutylamino-6-methyl-7-anilinofluoran | Di-(p-Methylbenzyl)oxalate | Synthesis Example 4 |
| 11 | 3-dibutylamino-6-methyl-7-anilinofluoran | 1,4-diprionyloxy benzene | Synthesis Example 4 |
| 12 | 3-dibutylamino-6-methyl-7-anilinofluoran | parabenzylbiphenyl | Systhesis Example 5 |
| 13 | 3-dibutylamino-6-methyl-7-anilinofluoran | parabenzylbiphenyl | Systhesis Example 6 |
| 14 | 3-dibutylamino-6-methyl-7-anilinofluoran | parabenzylbiphenyl | Systhesis Example 7 |
| 15 | 3-dibutylamino-6-methyl-7-anilinofluoran | parabenzylbiphenyl | Systhesis Example 8 |
| 16 | 3-dibutylamino-6-methyl-7-anilinofluoran | parabenzylbiphenyl | Systhesis Example 9 |
| 17 | 3-dibutylamino-6-methyl-7-anilinofluoran | parabenzylbiphenyl | Systhesis Example 10 |
| 18 | 3-dibutylamino-6-methyl-7-anilinofluoran | parabenzylbiphenyl | Systhesis Example 11 |
| 19 | 3-dibutylamino-6-methyl-7-anilinofluoran | parabenzylbiphenyl | Systhesis Example 12 |
| 20 | 3-dibutylamino-6-methyl-7-anilinofluoran | parabenzylbiphenyl | Systhesis Example 2 |
| 21 | 3-dibutylamino-6-methyl-7-anilinofluoran | parabenzylbiphenyl | Systhesis Example 13 |
| 22 | 3-dibutylamino-6-methyl-7-anilinofluoran | parabenzylbiphenyl | Systhesis Example 14 |
| 23 | 3-dibutylamino-6-methyl-7-anilinofluoran | parabenzylbiphenyl | Systhesis Example 1 |
| 24 | 3-dibutylamino-6-methyl-7-anilinofluoran | parabenzylbiphenyl | Synthesis Example 15 |
| 25 | 3-dibutylamino-6-methyl-7-anilinofluoran (75 parts) and 3-diethylamino-6-methyl-7-anilinofluoran (25 parts) | parabenzylbiphenyl | Synthesis Example 4 |
| 26 | 3-dibutylamino-6-methyl-7-anilinofluoran (50 parts) and 3-diethylamino-6-methyl-7-anilinofluoran (50 parts) | parabenzylbiphenyl | Synthesis Example 4 |
| 27 | 3-dibutylamino-6-methyl-7-anilinofluoran (25 parts) and 3-diethylamino-6-methyl-7-anilinofluoran (75 parts) | parabenzylbiphenyl | Synthesis Example 4 |
| 28 | 3-dibutylamino-6-methyl-7-anilinofluoran | 1,4-diprionyloxy benzene | Synthesis Example 5a |
| 29 | 3-dibutylamino-6-methyl-7-anilinofluoran | none | Synthesis Example 4 |
| 30 | 3-dibutylamino-6-methyl-7-anilinofluoran | 1,2-Bis(3,4-dimethylphenyl) ethane | Synthesis Example 4 |
| 31 | 3-dibutylamino-6-methyl-7-anilinofluoran | 1,2-Diphenoxyethane | Synthesis Example 4 |
| 32 | 3-dipentylamino-6-methyl-7-anilinofluoran | Di-(p-Methylbenzyl) oxalate | Synthesis Example 4 |
| 33 | 3-(N-ethyl-N-isoamylamino)-6-methyl-7-anilinofluoran | 1,2-Diphenoxyethane | Synthesis Example 4 |
| 34 | 3-(N-ethyl-N-isoamylamino)-6-methyl-7-anilinofluoran | Di-(p-Methylbenzyl) oxalate | Synthesis Example 4 |
| 35 | 3-(N-propyl-N-methylamino)-6-methyl-7-anilinofluoran | Di-(p-Methylbenzyl) naphthalene | Synthesis Example 4 |
| 36 | 3-dibutylamino-6-methyl-7-anilinofluoran | p-Tolylbiphenyl ether | Synthesis Example 4 |
| 37 | 3-(N-ethyl-N-isoamylamino)-6-methyl-7-anilinofluoran | 2-Benzyloxy naphthalene | Synthesis Example 4 |
| 38 | 3-dibutylamino-6-methyl-7-anilinofluoran | parabenzylbiphenyl | * |
| 39 | 3-dibutylamino-6-methyl-7-anilinofluoran | 2-Benzyloxy naphthalene | * |
| 40 | 3-(N-ethyl-N-isoamylamino)-6-methyI-7-anilinofluoran | 2-Benzyloxy naphthalene | * |
| 41 | 3-dipentylamino-6-methyl-7-anilinofluoran | Di-(p-Methylbenzyl) oxalate | * |
| 42 | 3-(4-diethylamino-2-ethoxyphenyl)-3-(1-octyl-2-methylindole-3-yl)-4-azaphthalide | Di-(p-Methylbenzyl) oxalate | * |
| 43 | 3-(4-diethylamino-2-ethoxyphenyl)-3-(1-octyl-2-methylindole-3-yl)-4-azaphthalide | parabenzylbiphenyl | 4 |
| 44 | 3-(4-diethylamino-2-ethoxyphenyl)-3-(1-octyl-2-methylindole-3-yl)-4-azaphthalide | 1,2-Diphenoxyethane | 4 |
| 45 | 3-(4-diethylamino-2-ethoxyphenyl)-3-(1-octyl-2-methylindole-3-yl)-4-azaphthalide | Ethyleneglycolbis-m-tolylether | 4 |
| 46 | 3-(4-diethylamino-2-ethoxyphenyl)-3-(1 -octyl-2-methylindole-3-yI)-4-azaphthalide | Di-(p-Methylbenzyl) oxalate | 4 |
| 47 | 3,3-bis(p-dimethylaminophenyl)-6-dimethylaminophthalide | parabenzylbiphenyl | 4 |
| 48 | 3-dibutylamino-6-methyl-7-anilinofluoran | N-phenyl phenyl sulphonamide | 4 |

*Developer used in conjunction with a stabiliser, formulation described below;

EXAMPLE 49

Preparation of Heat Sensitive Coating Formulations Containing N-(p-Toluenesulphonyl)-N'-(3-p-toluenesulphonyloxyphenyl)urea and a stabiliser Dispersions A to D were prepared by grinding the compositions shown below in an attritor until an average particle size of 1–1.5 $\mu$ was attained.

Dispersion A (Colour Former)

| | |
|---|---|
| 3-dibutylamino-6-methyl-7-anilinofluoran | 3.01 parts |
| Polyvinyl alcohol (10% aqueous solution) | 10.50 parts |
| Water | 6.49 parts |

Dispersion B (Colour Developer)

| | |
|---|---|
| N-(p-toluenesulphonyl)-N'-(3-p-toluenesulphonyloxyphenyl) urea | 7.5 parts |
| Polyvinyl alcohol (10% aqueous solution) | 7.5 parts |
| Water | 22.5 parts |

Dispersion C (Sensitiser)

| | |
|---|---|
| parabenzylbiphenyl | 10.0 parts |
| Polyvinyl alcohol (10% aqueous solution) | 10.0 parts |
| Water | 20.0 parts |

Dispersion D (Stabiliser)

| | |
|---|---|
| 1,1,3-tris(3'-cyclohexyl-4'-hydroxy-6'-methylphenyl)butane | 7.5 parts |

-continued

| | |
|---|---|
| Polyvinyl alcohol (10% aqueous solution) | 7.5 parts |
| Water | 22.5 parts |

A thermal coating mixture was then prepared by combining together the following components:

| | parts by weight |
|---|---|
| Dispersion A | 6.6 |
| Dispersion B | 10.0 |
| Dispersion C | 6.0 |
| Dispersion D | 2.5 |
| Calcium Carbonate (25% aqueous dispersion) | 12.0 |
| Zinc stearate (33% aqueous dispersion) | 0.9 |
| Polyvinyl alcohol (10% aqueous solution) | 4.5 |
| Tinopal ® ABP-X (fluorescent whitening agent) | 0.12 |
| Water | 2.48 |

This coating mixture was applied on one side of a base paper weighing 50 g/m² in a coating weight of about 5.0 g/m² and then dried. The resulting sheet was calendered by means of a laboratory calender to produce a recording sheet with excellent background whiteness.

What is claimed is:

1. A compound of the formula $$R_1-\underset{\underset{O}{\|}}{\overset{\overset{O}{\|}}{S}}-\underset{H}{N}-X-\underset{H}{N}-\underset{R_4}{\overset{R_3}{\bigcirc}}-B-R_2 \quad (2)$$

wherein $R_1$ is unsubstituted or substituted phenyl, or naphthyl, $R_3$ and $R_4$ independently of each other are hydrogen, $C_1-C_8$alkyl, halogen-substituted $C_1-C_8$alkyl, $C_1-C_8$alkoxy-substituted $C_1-C_8$alkyl, $C_1-C_8$alkoxy, halogen-substituted $C_1-C_8$alkoxy, $C_1-C_8$alkylsulphonyl, halogen, phenyl, phenoxy or phenoxycarbonyl, X is a group of the formula $$-\overset{NH}{\underset{\|}{C}}-, \quad -\overset{S}{\underset{\|}{C}}- \quad \text{or} \quad -\overset{O}{\underset{\|}{C}}-,$$

B is a linking group of formula $-O-SO_2-$, $-SO_2-O-$, $-SO_2-NH-$, or $-CO-NH-SO_2-$, and $R_2$ is phenyl, which is unsubstituted or substituted by $C_1-C_8$alkyl, halogen-substituted $C_1-C_8$alkyl, $C_1-C_8$alkoxy-substituted $C_1-C_8$alkyl, $C_1-C_8$alkoxy, halogen-substituted $C_1-C_8$alkoxy or halogen; naphthyl and benzyl, which is substituted by $C_1-C_4$alkyl or halogen, with the proviso, that, if B is not a linking group of formula $-O-SO_2-$, $R_2$ is unsubstituted or substituted phenyl, or naphthyl.

2. A compound according to claim 1, wherein $R_1$ is phenyl, which is substituted by $C_1-C_4$alkyl, X is a group of the formula $$-\overset{O}{\underset{\|}{C}}-,$$

$R_3$ and $R_4$ independently of each other are hydrogen, $C_1-C_4$alkyl or halogen B is a linking group of formula $-O-SO_2-$, and $R_2$ is phenyl, which is unsubstituted or substituted by $C_1-C_4$alkyl.

3. A heat sensitive recording material, comprising a) at least one colour forming compound, and b) at least one developer of the formula $$R_1-\underset{\underset{O}{\|}}{\overset{\overset{O}{\|}}{S}}-\underset{H}{N}-X-\underset{H}{N}-A-B-R_2 \quad (1)$$

wherein $R_1$ is phenyl or naphthyl, which can be unsubstituted or substituted by $C_1-C_8$alkyl, $C_1-C_8$-alkoxy or halogen, X is a group of the formula $$-\overset{NH}{\underset{\|}{C}}-, \quad -\overset{S}{\underset{\|}{C}}- \quad \text{or} \quad -\overset{O}{\underset{\|}{C}}-,$$

A is unsubstituted or substituted phenylene, naphthylene or $C_1-C_{12}$alkylene, or is an unsubstituted or substituted heterocyclic group, B is a linking group of formula $-O-SO_2-$, $-SO_2-O-$, $-NH-SO_2-$, $-SO_2-NH-$, $-S-SO_2-$, $-O-CO-NH-$, $-NH-CO-$, $-NH-CO-O-$, $-S-CO-NH-$, $-S-CS-NH-$, $-CO-NH-SO_2-$, $-O-CO-NH-SO_2-$, $-NH=CH-$, $-CO-NH-CO-$, $-S-$, $-CO-$, $-O-$, $-SO_2-NH-CO-$, $-O-CO-O-$ and $-O-PO-(OR_2)_2$, and $R_2$ is phenyl, which is unsubstituted or substituted by $C_1-C_8$alkyl, halogen-substituted $C_1-C_8$alkyl, $C_1-C_8$alkoxy-substituted $C_1-C_8$alkyl, $C_1-C_8$alkoxy, halogen-substituted $C_1-C_8$alkoxy or halogen; naphthyl and benzyl, which is substituted by $C_1-C_4$alkyl or halogen, with the proviso, that, if B is not a linking group of formula $-O-SO_2-$, $R_2$ is unsubstituted or substituted phenyl or naphthyl.

4. A recording material according to claim 3, wherein $R_1$ is phenyl which is unsubstituted or substituted by $C_1-C_8$alkyl, $C_1-C_8$alkoxy or halogen.

5. A recording material according to claim 3, wherein $R_1$ is phenyl which is substituted by $C_1-C_8$alkyl, $C_1-C_8$alkoxy or halogen.

6. A recording material according to claim 3, wherein $R_1$ is phenyl which is substituted by $C_1-C_4$alkyl.

7. A recording material according to claim 3, wherein X is a group of the formula

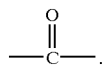

8. A recording material according to claim 3, wherein
A is phenylene which is unsubstituted or substituted by $C_1$–$C_8$alkyl, halogen-substituted $C_1$–$C_8$alkyl, $C_1$–$C_8$alkoxy-substituted $C_1$–$C_8$alkyl, $C_1$–$C_8$alkoxy, halogen-substituted $C_1$–$C_8$alkoxy, $C_1$–$C_8$alkylsulphonyl, halogen, phenyl, phenoxy or phenoxycarbonyl; or is naphthylene; or $C_1$–$C_{12}$alkylene; or pyrimidylene which is unsubstituted or substituted by $C_1$–$C_8$alkyl.

9. A recording material according to claim 8, wherein
A is phenylene which is unsubstituted or substituted by $C_1$–$C_8$alkyl, halogen-substituted $C_1$–$C_8$alkyl, $C_1$–$C_8$alkoxy-substituted $C_1$–$C_8$alkyl, $C_1$–$C_8$alkoxy, halogen-substituted $C_1$–$C_8$alkoxy, $C_1$–$C_8$alkylsulphonyl, halogen, phenyl, phenoxy or phenoxycarbonyl.

10. A recording material according to claim 9, wherein A is phenylene which is unsubstituted or substituted by $C_1$–$C_8$alkyl, halogen-substituted $C_1$–$C_8$alkyl, $C_1$–$C_8$alkylsulphonyl or halogen.

11. A recording material according to claim 10, wherein A is phenylene which is unsubstituted or substituted by $C_1$–$C_4$alkyl or halogen.

12. A recording material according to claim 11, wherein A is unsubstituted phenylene.

13. A recording material according to claim 3, wherein B is a linking group of formula —O—$SO_2$—, —$SO_2$—O—, —$SO_2$—NH—, —S—$SO_2$—, —O—, —O—CO—NH—, —$SO_2$—NH—CO—, —O—CO—O— or —O—PO—$(OR_2)_2$.

14. A recording material according to claim 13, wherein B is a linking group of formula —O—, —O—$SO_2$—, —$SO_2$—O— or —$SO_2$—NH—.

15. A recording material according to claim 14, wherein B is a linking group of formula —O—$SO_2$—.

16. A recording material according to claim 14, wherein B is a linking group of formula —O— and $R_2$ is unsubstituted or substituted aryl or benzyl.

17. A recording material according to claim 3, wherein $R_2$ isphenyl, which is unsubstituted or substituted by $C_1$–$C_4$alkyl or halogen; naphthyl or benzyl, which is unsubstituted or substituted by $C_1$–$C_4$alkyl or halogen.

18. A recording material according to claim 3, wherein $R_2$ is phenyl, which is unsubstituted or substituted by $C_1$–$C_4$alkyl.

19. A recording material according to claim 3, wherein $R_1$ is phenyl which is substituted by $C_1$–$C_4$alkyl, X is a group of the formula

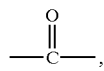

A is phenylene which is unsubstituted or substituted by $C_1$–$C_4$alkyl or halogen,
B is a linking group of formula —O—$SO_2$— or —O—, and $R_2$ is phenyl or benzyl which is unsubstituted or substituted by $C_1$–$C_4$alkyl.

20. A recording material according to claim 3, wherein the recording material comprises at least one sensitiser.

21. A recording material according to claim 20, wherein the recording material comprises at least one sensitizer selected from the group consisting of stearamide, methylol stearamide, p-benzylbiphenyl, m-terphenyl, 2-benzyloxynaphthalene, 4-methoxybiphenyl, dibenzyl oxalate, di(4-methylbenzyl) oxalate, di(4-chlorobenzyl) oxalate, dimethyl phthalate, dibenzyl terephthalate, dibenzyl isophthalate, 1,2-diphenoxyethane, 1,2-bis(4-methylphenoxy) ethane, 1,2-bis(3-methyl-phenoxy)ethane, 4,4'-dimethylbiphenyl, phenyl-1-hydroxy-2-naphthoate, 4-methylphenyl biphenyl ether, 1,2-bis(3,4-dimethylphenyl) ethane, 2,3,5,6–4'-methyldiphenyl methane, 1,4-diethoxy-naphthalene, 1,4-diacetoxybenzene, 1,4-diproprionoxybenzene, o-xylylene-bis(phenyl ether), 4-(m-methylphenoxymethyl) biphenyl, p-hydroxyacetanilide, p-hydroxybutyranilide, p-hydroxynonananilide, p-hydroxylauranilide, p-hydroxyoctadecananilide, N-phenyl-phenylsulphonamide and sensitizers of the formula

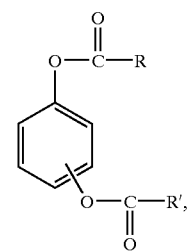

(3)

wherein R and R' are identical or different from each other and each represent $C_1$–$C_6$alkyl.

22. A recording material according to claim 3, wherein the recording material comprises at least one stabiliser.

23. A recording material according to claim 22, wherein the recording material comprises at least one stabiliser selected from the group consisting of 2,2'-methylene-bis(4-methyl-6-tert-butylphenol), 2,2'-methylene-bis(4-ethyl-6-tert-butylphenol), 4,4'-butylidene-bis(3-methyl-6-tert-butylphenol), 4,4'-thio-bis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl)butane, bis (3-tert-butyl-4-hydroxy-6-methylphenyl)sulfone, bis(3, 5-dibromo-4-hydroxyphenyl) sulfone, 4,4'-sulfinyl bis (2-tert-butyl-5-methylphenol), 2,2'-methylene bis(4,6-di-tert-butylphenyl) phosphate and alkali metal, ammonium and polyvalent metal salts thereof, 4-benzyloxy-4'-(2-methylglycidyloxy)diphenyl sulfone, 4,4'-diglycidyloxydiphenyl sulfone, 1,4-diglycidyloxybenzene, 4-[α-(hydroxymethyl)benzyloxy]-4-hydroxydiphenyl sulfone, metal salts of p-nitrobenzoic acid, metal salts of phthalic acid mono benzyl ester, metal salts of cinnamic acid and mixtures thereof.

* * * * *